United States Patent

Knospins

[11] Patent Number: 4,867,681
[45] Date of Patent: Sep. 19, 1989

[54] METHOD OF SECURING MAT ADHESIVES TO DENTURES

[76] Inventor: Alfred Knospins, 2 Alice Ct., Poughkeepsie, N.Y. 12603

[21] Appl. No.: 166,073
[22] Filed: Mar. 9, 1988
[51] Int. Cl.⁴ ............................................. A61C 13/12
[52] U.S. Cl. ................................. 433/180; 433/168.1
[58] Field of Search ..................... 433/168.1, 180, 171, 433/169, 167, 172

[56] References Cited

U.S. PATENT DOCUMENTS

| 167,336 | 8/1875 | Hickman | 433/168.1 |
| 2,817,900 | 12/1957 | Glasser | 433/168.1 |
| 4,503,116 | 3/1985 | Lapidus | 433/180 |

FOREIGN PATENT DOCUMENTS

| 7775 | of 1893 | United Kingdom | 433/168.1 |
| 424587 | 2/1935 | United Kingdom | 433/168.1 |

Primary Examiner—John J. Wilson
Assistant Examiner—Adriene J. Lepiane
Attorney, Agent, or Firm—Pollock, Vande Sande & Priddy

[57] ABSTRACT

Method for securing an insert to a denture. A sheet of standard denture adhesive, which conforms to the denture gum-receiving surface is overlaid over the gum-receiving surface. The dentures are predrilled at the ends thereof with holes to permit fastening of the ends of the adhesive material to the denture. By using a standard household polyester thread and needle, it is possible to sew the ends of the adhesive material to the first and second denture ends, maintaining the adhesive material ends in proper relationship with the denture, and preventing slippage.

4 Claims, 1 Drawing Sheet

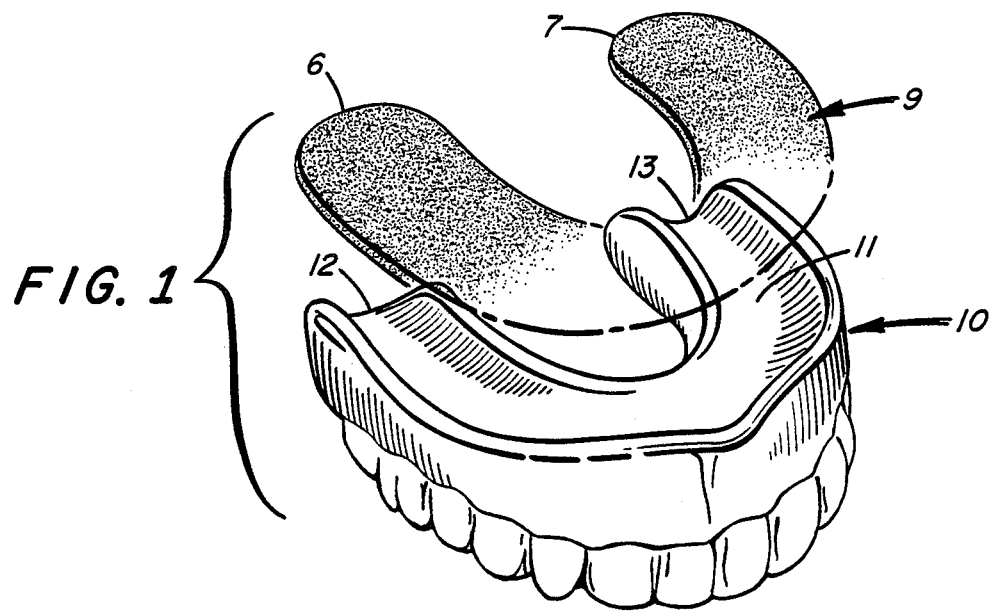
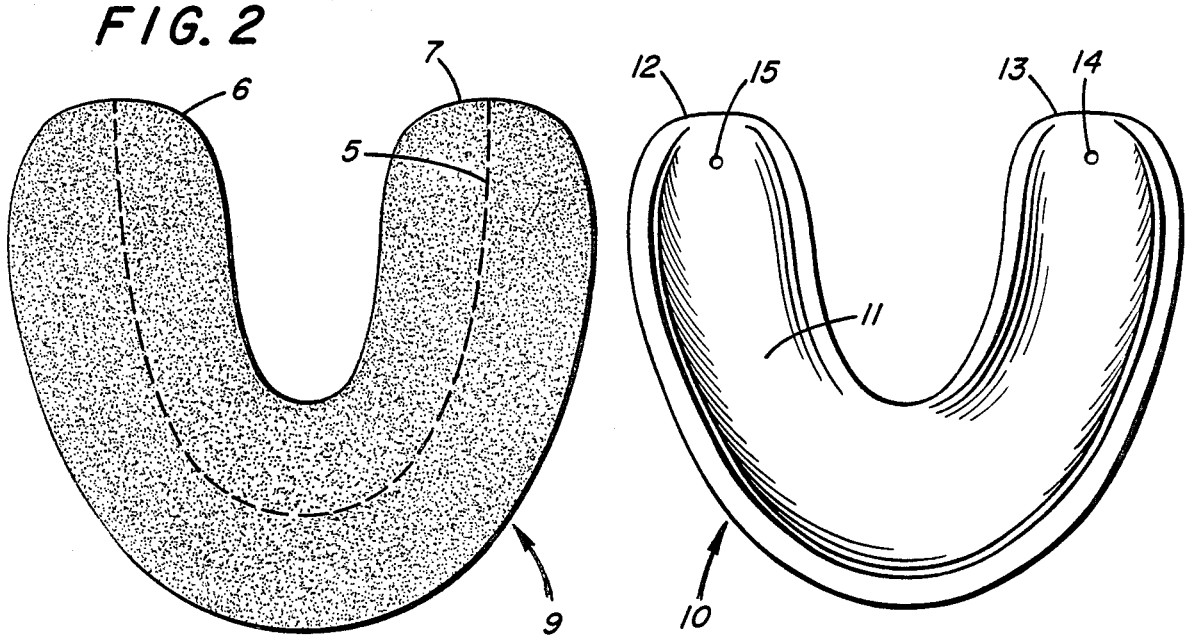
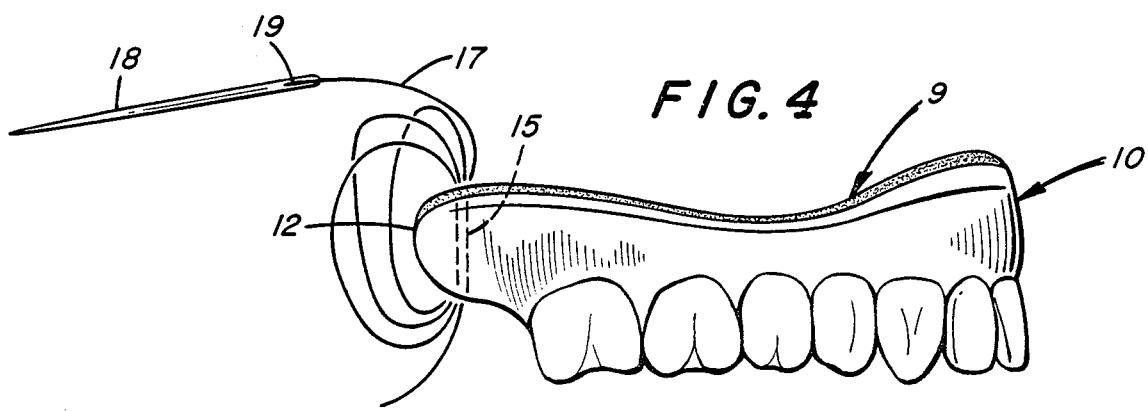

METHOD OF SECURING MAT ADHESIVES TO DENTURES

BACKGROUND OF THE INVENTION

The present invention relates to denture devices. Specifically, a method for securing denture adhesive to a denture and maintaining the adhesive positioned relative to the denture is described.

The interface between the human gum and dentures has been the subject of much investigation by the manufacturers of prosthetic devices. The coupling between human tissue and prosthetic devices must be uniform and tight in order to prevent food particles from getting between the gum and denture, making the user uncomfortable.

Among the various adhesives used in the past as a coupling agent between the gum and denture are compressed fiber mats which contain a water-activated adhesive. One such adhesive is described in U.S. Pat. No. 4,503,116, and is generally sold to the public as Sea Bond Dental Adhesive. These materials are cut in the proper conforming shape to line the inside surface of the denture. The adhesive and denture are then properly fitted into place.

Unfortunately, the mat-like adhesive materials are subject to slippage, thus disturbing the coupling between gum and denture. Various techniques have been suggested in the past for reducing this slippage. These are represented in U.S. Pat. Nos. 167,336; 126,809 and 2,817,900, as well as British Patent Specification No. 424,587, and British Patent No. 7775, dated Apr. 25, 1892.

These references seek to avoid the slippage problem by employing various fastening devices, such as screws, rivets, posts and pins, maintaining the soft gasket material in position. The presence of these fastening devices produces discomfort to the user and may interfere with the coupling between the denture and gum. Additionally, these fastening devices may promote bacteria growth and otherwise be unhealthy to the user.

SUMMARY OF THE INVENTION

It is an object of this invention to secure an adhesive mat to a denture.

It is a more specific object of this invention to provide a method for easily and hygenically maintaining an adhesive mat positioned with respect to a denture.

These and other objects of the invention are provided by a method which is hygenic and easy to implement by any denture wearer. Commercially available adhesive mat material is used to cover the interior surface of the denture which faces the gum. The mat material is applied in a conventional way.

The dentures have located at first and second ends a small hole of a diameter sufficient to receive several strands of thread. These holes permit the ends of the conforming mat material to be secured to the ends of the dentures.

In carrying out the method according to a preferred embodiment of the invention, a household sewing needle and length of polyester thread is used to sew the mat adhesive to the denture ends by passing the thread through the holes and wrapping around the denture and mat adhesive. Several wraps are provided and then tied off to prevent slippage of the mat material within the denture.

BRIEF DESCRIPTION OF THE FIGURES

FIG. 1 illustrates the relationship between a mat-type adhesive and an upper denture.

FIG. 2 illustrates the form of the mat-type adhesive used in the method of the invention.

FIG. 3 illustrates the required two holes which are drilled in the ends of the denture.

FIG. 4 illustrates the step of securing of the adhesive mat material to the denture.

DESCRIPTION OF A PREFERRED EMBODIMENT

Referring now to FIG. 1, there is shown the relationshp between a denture 10 and a mat adhesive material 9. The mat adhesive material 9 may be a commercially available denture adhesive sold under the name Sea Bond, manufactured by Combe, Inc. This denture adhesive is a mat material of a cellulose, paper-thin insert. These inserts are normally sold without any provision for securing to the inner surface 11 of the denture 10. The inner gum-receiving surface 11 is lined with the denture adhesive 9 so that the denture adhesive 9 conforms to the gum-receiving surface 11.

During use of these otherwise excellent denture adhesives, the ends 6 and 7 will tend to slip and separate from the corresponding ends 12 and 13 of the denture 10. The slippage causes discomfort to the user during mealtime. The required seal between the human gums and denture interior 11 is not maintained, requiring a resetting of the material.

In order to avoid the foregoing problem of slippage, the material shown in FIG. 2 may be fastened to the denture in a way which will prevent the ends 6 and 7 from separating from the ends 12 and 13 of the denture 10.

Referring to FIG. 3, the ends 12 and 13 of the denture 10 are shown to include two small holes 14 and 15. These holes may be advantageously 1 mm in diameter, and spaced from the ends 12 and 13 a distance of 3 mm. The denture adhesive 9 is conformed to the interior gum-receiving surface 11 of the denture by folding along a line 5 shown in FIG. 2. The fold, represented by line 5, will aid in aligning the denture adhesive 9 with respect to the interior surface 11.

Once the gum-receiving surface 11 is lined with the denture adhesive 9, the user may advantageously fasten the ends 6 and 7 to ends 12 and 13 of the denture 10.

Referring to FIG. 4, the simplest and hygenically acceptable way of fastening the ends of the denture adhesive 9 to the ends 12 and 13 of the denture 10 is by using a household needle and thread. The hole 15 is threaded with the needle 18 and thread, fastened through the eyelet 19 in the conventional way, through at least three and preferably four wraps through the denture material 9, and around the exterior end 12 of the denture. Three or more stitches are made, thus securing the end 6 of the denture adhesive to the denture end 12. The thread, which may be a standard household polyester thread, is tied off securely in a way which will not interfere with the adhesive denture gum bond.

The end 7 of the adhesive material 9 is similarly sewn by needle and thread, and tied off. The entire assembly may be conveniently washed under a faucet before insertion into the mouth.

It has been found that the foregoing technique will maintain the ends 6 and 7 positioned with regard to the denture 10 ends 12 and 13 for a longer period of time than has heretofore been possible. No possible contamination or unhealthy side effects result from having the thread bonding the ends of the dental adhesive to the denture. Of course, it is possible to peiodically remove the stitches, pemitting cleaning of the denture and insertion of a new dental adhesive in a convenient manner.

The presence of the thread stitches does not provide any discomfort to the wearer who is hardly aware of this presence, but enjoys the additional extended use of an otherwise excellent dental adhesive.

The foregoing is one example of a technique in accordance with the claims which follow which will benefit denture wearers.

What is claimed is:

1. A method for securing an insert to a denture comprising:

pre-drilling first and second holes in first and second denture ends;
 forming from a sheet of denture adhesive material a conforming strip of adhesive for inserting between a denture surface and a user's gum;
 overlaying said conforming strip of adhesive material over said denture; and,
 securing first and second ends of said adhesive material to said first and second denture ends by passing a thread through said holes and about said denture ends a plurality of times, wrapping said denture ends and denture adhesive ends, whereby said adhesive material ends are maintained in proper position and prevented from slipping in relationship to said denture.

2. The method of claim 1 wherein said thread is polyester.

3. The method of claim 1 wherein said holes are located approximately 3 mm from the rear edges of said dentures.

4. The method of claim 3 wherein said holes are approximately 1 mm in diameter.

* * * * *